United States Patent [19]

Huebscher et al.

[11] 4,324,258

[45] Apr. 13, 1982

[54] ULTRASONIC DOPPLER FLOWMETERS

[76] Inventors: Werner Huebscher, Buenstrasse 10, 8600 Dübendorf; Max Anliker, Schlösslistr. 22, 8044 Zuerich, both of Switzerland

[21] Appl. No.: 162,668

[22] Filed: Jun. 24, 1980

[51] Int. Cl.³ ............................................. A61B 10/00
[52] U.S. Cl. .................................. 128/663; 73/861.25
[58] Field of Search .................... 128/663; 73/861.25; 343/5 DP; 307/354

[56] References Cited

PUBLICATIONS

Brandestini, M. "Topoflow-A Digital Full Range Doppler Velocity Meter", IEEE Trans. on Sonics & UTS, vol. SU-25, #5, Sep. 1978, pp. 287-293.
Brandestini, M. et al., "Blood Flow Imaging Using a Discrete-Time Frequency Meter", 1978 UTS Symp. Proc., Cherry Hill, N.J., 25-27 Sep. 1978.
Brandestini, M., "A Digital 128-Channel Transcutaneous Blood Flowmeter", Biomedizinische Technik, vol. 21, pp. 291-292, Jun. 1976.

*Primary Examiner*—Robert W. Michell
*Assistant Examiner*—Francis J. Jaworski

*Attorney, Agent, or Firm*—Blakely, Sokoloff, Taylor & Zafman

[57] ABSTRACT

In an ultrasonic Doppler flowmeter system for the measurement, imaging and mapping of blood flow, a transducer coupled to a patient's skin is caused to emit pulses of high frequency ultrasound waves. The resulting echo signals are received by the transducer, demodulated into quadrature components, sampled into a large plurality of channels, and digitized. An improved stationary filter circuit utilizing a finite iteration then suppresses unwanted masking "clutter", i.e., low frequency but large amplitude signals from stationary tissue interfaces, with significantly improved response time and dynamic range, while providing good resolution. The Doppler frequency period of the moving acoustic scatterers is obtained by passing the remaining signal through a zero crossing detector. A sign detector circuit separates the multiplexed quadrature components and compares them to each other to determine the direction of the flow, while extending the Doppler bandwidth to assure compliance with the Nyquist criteria for sampled systems. A frequency to velocity converter then generates a voltage proportional to the Doppler velocity for each sample channel. These velocity values enable outputs in various forms, for example, blood flow profiles.

10 Claims, 6 Drawing Figures

ULTRASONIC DOPPLER FLOWMETERS

DESCRIPTION

This invention relates generally to ultrasound imaging of internal structures and fluids, and more specifically, to improvements in the measurement, imaging and mapping, by use of the Doppler principle, of the movement and flow of internal body fluids, especially blood, and the vessels containing such flow, for example, blood vessels and heart walls.

BACKGROUND OF THE INVENTION

Ulrasonic technology has in recent years become ever more important in medical diagnosis. Such technology finds application where it is desired to examine internal body organs and fluids with the objective of locating features or aspects which may be indicative of disease or absnormalities. Typical instruments detect the amplitude of the echo signals returning from the structure being examined, and usually display the information in a two-dimensional "B Scan" image. Less common, and less straightforward, is the detection of velocity along the axis of the interrogating sound beam, rather than amplitude. Such detection can provide an image of the blood flow pattern, or vessel network, information of high diagnostic significance. The detection of velocity is based upon the Doppler principle, whereby a change in observed frequency of the reflected echo pulse is indicative of a corresponding change in the velocity in the region from which the echo emanates.

Fortunately, much basic work on such Doppler based flowmeter systems has already been done. A basic system is described in M. Anliker, titled "Current and Future Aspects of Biomedical Engineering", *Triangle*, Volume 16, No. 1, 1977, 129, 130-132. Another later system of the type is described in M. Brandestini, "Topoflow-A Digital Full Range Doppler Velocity Meter", IEEE Transactions in Sonics and Ultrasonics, Volume SU-25, No. 5, September 1978, Pages 288-291. Other similar papers are "Blood Flow Imaging Using a Discrete Time Frequency Meter", Brandestini and Forrester, 1978 Ultrasonic Symposium Proceedings, IEEE Catalog 78CH1344-ISU and F. D. McLeod, M. Anliker, "A Multiple Gate Pulsed Directional Doppler Flowmeter, Proceedings IEEE Ultrasonic Symposium," Miami, December 1971; and F. E. Barber, D. W. Baker, D. E. Strandness Jr. and G. D. Mahler, "Duplex Scanner II", Ultrasonic Symposium Proceeding, IEEE Catalog 74, CHO08961SU, 1974.

Most of the prior Doppler systems involve an RF ultrasonic pulse transmitting and receiving section, and some form of quadrature phase detection, transmitting by means of a transducer an interrogating pulse train into the structure under examination and receiving and resulting echo information for processing. The RF frequency is of the order of megacycles, while the pulse repetition frequencies are typically in the kilohertz range. Thus, a pulse repetition interval of 100 to 200 microseconds between pulses may be expected, and a useful range of no more than 10 to 20 centimeters into the patient's body. Along with the received actual echo signal, the quadrature echo signal, accomplished by mixing with a local oscillator signal differing in phase by 90° from the transmitter frequency, preserves phase and the ability to later detect the sign, i.e., flow direction, of the fluid movement under examination.

The next section typically found in such Doppler systems usually involves the sampling of the Doppler information-carrying envelope with both the original and orthogonal detected echo signal into a number of channels similar to the number of microseconds interval between the pulses, typically into 128 channels. Of course, each such channel or portion of the time interval between pulses also corresponds to a portion or interval of a range within the patient's body under interrogation. If structures or fluids in any such interval within the body have a velocity component in the direction of the axis of ultrasonic radiation, a Doppler frequency change is impressed upon the echo emanting from such interval or channel.

However, complicating the detection of such Doppler frequencies is the existence of quasi-specular stationary reflecting tissue interfaces which yield echo signals of large amplitudes, thus masking the much lower amplitude signals scattered by the moving blood cells, and which actually contain Doppler information of interest. The difference in amplitude may be as much as two orders of magnitude. Such large echo "clutter" signals, being from stationary interfaces, have no Doppler information, and change little, if at all, from one interrogating pulse to the next, while the echo signals from moving scatterers such as blood will change rapidly. It was realized that decomposing the received echo signals into the large, but relatively fixed, clutter components, and a small, rapidly-changing signal component could provide the key to resolving this masking problem.

Accordingly, as the next stage of some Doppler systems, certain investigators, (especially Anliker and Brandestini), utilized analog/digital recursive stationary canceler-filters based on principles first utilized in radar in order to digitize the incoming signals and remove therefrom those components from fixed tissue interfaces, and low-pass filter the non-blood flow low-frequency Doppler signals from such reflectors as moving lumen walls. Such filters attempted to split the analog digital version of the sampled echo signals into a "fast" and a "slow" section, and utilized a tracking type conversion relying on the Doppler difference between subsequent pulses to track and eliminate clutter, since it is nearly constant from pulse to pulse, while attempting to digitize with maximum speed the small-amplitude, but fast-changing Doppler portion of the system remaining after subtraction of the clutter.

Such digital canceller-filters, while a substantial improvement over prior expedients, nevertheless have not performed well enough to enable Doppler flowmeter systems to function at practical levels, with performance levels sufficient to provide truly acceptable commercial instruments. Rather severe demands on such filters result from the fact that not only are the amplitude changes in the echoes as much as two orders of magnitude different, but also such changes are very sudden, and may cause transfer of low frequency energy content into neighboring channels. The handling of such large-amplitude changes obviously requires a high degree of resolution and dynamic range, and the suddenness of such changes further requires short response times, if substantial amounts of Doppler information-bearing echo signals are not to be lost under the influence of clutter signal amplitudes, and because of the time required for the filter to respond and to eliminate same. In these respects, the stationary filter-cancellers of the prior art have been less than satisfactory, and have been found lacking, especially in the dynamic range and response time necessary to perform at a sufficient resolution level.

The filter-canceller stage has then typically supplied the input for a zero crossing detector and a companion flow velocity sign detector circuit. The function of the crossing detector is to detect the zero crossings which the Doppler signal undergoes over a period of time in one direction for each channel, which then gives the measure of the Doppler frequency. The sign detector is important in determining whether a positive or negative Doppler shift is occurring within each channel. This is critical for the operation of the conventional Doppler frequency to velocity converter with which these systems are finally equipped, and which then yield a velocity for each channel. Such converters accumulate over some predetermined time period counts corresponding to the occurrence of zero crossings for each channel, and must be instructed as to whether the zero crossing is in one sense or the opposite sense, that is, whether the count should be added or subtracted. The sign detector, by comparing quadrature components through which phase information has been preserved, and obtaining the instantaneous direction of the Doppler frequency, supplies such instruction to the velocity converter.

Again, while such zero crossing detectors and sign detector means have been the best expedients heretofore available, they, too, have had serious shortcomings. These have primarily to do with the inherent limitations of sample systems, in particular as imposed by the well-known Nyquist criterion. In other words, in quadrature multiplexed systems, it is well-known that when the detected frequency exeeds one-quarter the repetition rate of the interrogating acoustic pulse, the phase information can no longer be preserved. Thus, while the fact of a zero crossing may be reliably detected in such prior art expedients, its direction will not be reliably detected, under the foregoing conditions. Therefore the operation of any Doppler frequency to velocity converter in the prior art under these circumstances is correspondingly also unreliable and unsatisfactory.

Accordingly, it may be regarded as an object of the present invention to provide a Doppler flowmeter system with improved resolution, dynamic range and response time to enable a practical level of performance in measuring the flow of body fluids.

It is a further object of the invention to provide a Doppler system with an improved digital stationary canceler-filter for a Doppler flowmeter system having improved dynamic range and response time at high resolution level.

It is a still further object of the invention to provide a Doppler system with improved zero crossing and sign detector circuits having an extended Doppler bandwidth for improved handling of sampled echo information to assure satisfying the Nyquist criterion.

SUMMARY OF THE INVENTION

The foregoing objects of the invention are met by providing an improved sampled ultrasonic system utilizing the Doppler principle which measures the velocity of fluids moving within internal body structures. The system includes means for transmitting an acoustic beam comprised of addressing pulses of ultrasonic-frequency acoustic waves having a regular pulse repetition rate into the body structure under consideration, and for receiving the acoustic echo energy from both stationary and moving acoustic scatterers within the path of the beam, and finally converting same into corresponding electrical echo signals. The echo signals, which contain both Doppler and stationary echo information, are also demodulated into quadrature echo signals in order to preserve phase change information imparted by the moving scatterers. Means are provided for sampling the quadrature echo signals into a plurality of equal channels, each corresponding to a portion of the time between addressing pulses. Each channel then also corresponds to an equal portion of the overall range of the addressing pulse within the body. This system also includes filter means accepting the quadrature echo signals and canceling therefrom any stationary non-Doppler information. Also provided are means for determining from the digitized form of the remaining Doppler echo information the velocity of the fluids under interrogation.

In accordance with one particular aspect of the invention, the filter, inserted between the means for sampling and the velocity determining means, and servicing each of the channels, employs a recursive loop including a digital memory for comparing the echo signals from each addressing pulse with the immediately proceeding echo signal, a subtractor to subtract any unchanged non-Doppler components for a given channel, and an analog digital converter rapidly digitizing the remaining changing components of the echo signal. Such a recursive filter requires a definite number of iterations in order to handle large amplitude stationary echo signals which are reflected, for example, from vessel walls, and which mask the much lower amplitude signals containing Doppler information from moving body fluids within such vessels. The time required for the filter to respond to such situations detracts from the filter's ability to "see" Doppler information bearing signals, which may then be lost. Accordingly, response time is greatly improved by a comparator means in parallel with said analog/digital converter, for identifying the highest active digital bit between the digital dynamic range of the incoming echo signal, and the dynamic range of the analog/digital converter, said comparator providing said highest active bit to be added along with the output of said analog/digital converter into said memory, so that upon subsequent comparison with incoming echo signals for said given channel, subtraction therefrom, and subsequent further iterations thereof, the number of iterations is decreased, and the response time is correspondingly improved for large stationary echo signals. In this manner, the dynamic range, response time, and resolution of the system is greatly improved as compared to earlier expedients.

In accordance with a further aspect of the invention, means are provided in the system for determining, from the signal which remains after processing by the filter and which comprises Doppler echo information in digital form, the zero crossings in one direction of said signal, in order to obtain the Doppler frequency for each channel. This information is directed to the means for determining the fluid velocity, which also requires instruction as to whether the sign of the Doppler frequency shift is positive or negative, and which includes means accumulating digital counts representative of the zero crossings. Supplying such instruction as to the direction of the Doppler shift is a means for determining the sign of the Doppler shift. This means includes means for comparing the quadrature component of the quadrature echo signals to determine the instantaneous sign of the Doppler frequency shift for each channel. Also included is means for comparing the accumulated counts within the frequency to velocity converter against a predetermined frequency (the Nyquist criterion), and upon said counts exceeding the value corresponding thereto, substituting the sign of the velocity determined just prior to said value being exceeded, in preference to said instantaneous sign. In this manner, the limitations of the sampled system in accurately detecting the direction of the Doppler frequency shift, and consequently accurately determining the velocity, are obviated within the ranges which concern human diagnostic needs. It is well known that quadrature sampled systems such as the foregoing are normally limited because of the Nyquist criterion. Thus, if the accumulated count of a channel indicates a Doppler frequency above this criterion of one-quarter the addressing pulse repetition frequency, it is well-known that phase can no longer preserved, and thus, the usual sign detector instruction to the frequency to velocity converter as to whether to add or subtract pulses representative of zero crossings is no longer reliable. The foregoing arrangement overcomes these limitations to a substantial extent, and in effect extends the bandwidth of the system to accommodate Doppler bandwidths normally beyond the Nyquist criterion.

DETAILED DESCRIPTION OF THE PREFERRED EMBODIMENT

Figure 1:
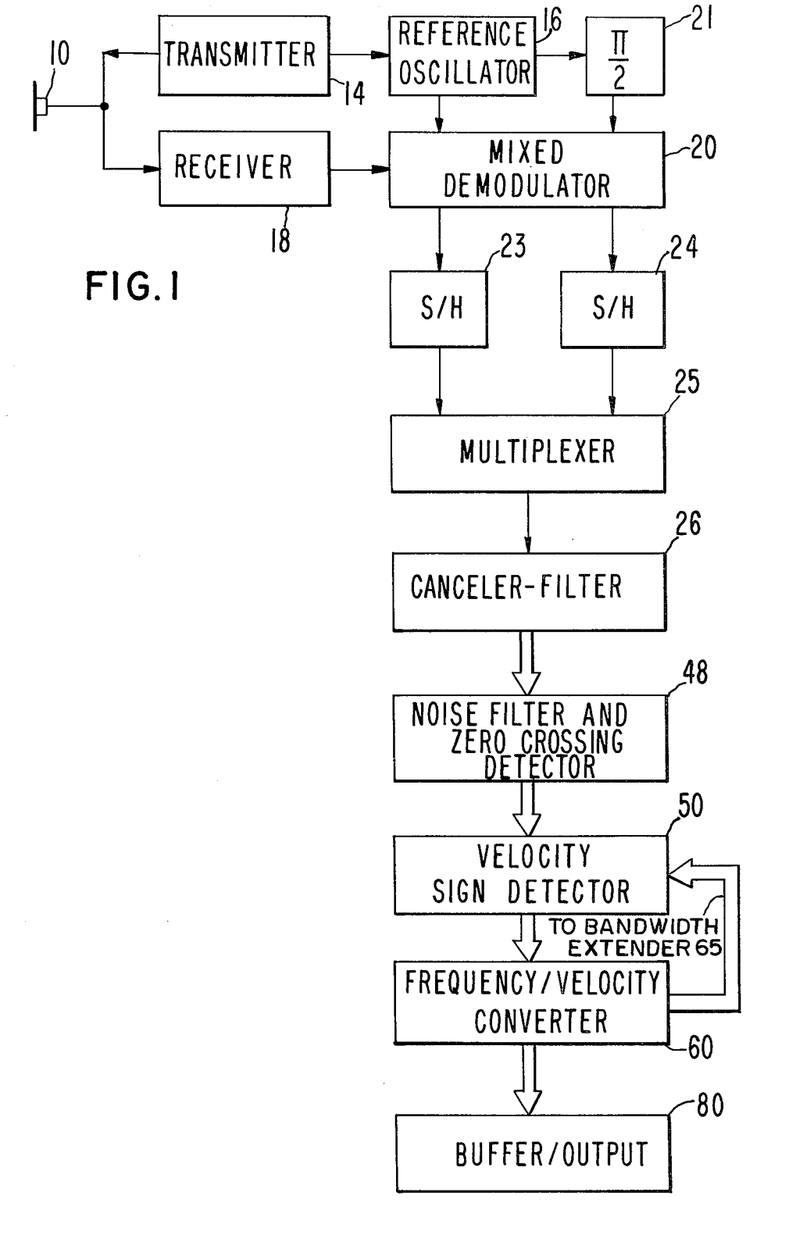
FIG. 1 is an electrical block diagram schematic illustrating an improved ultrasonic Doppler flowmeter system in accordance with the present invention.
Figure 2:
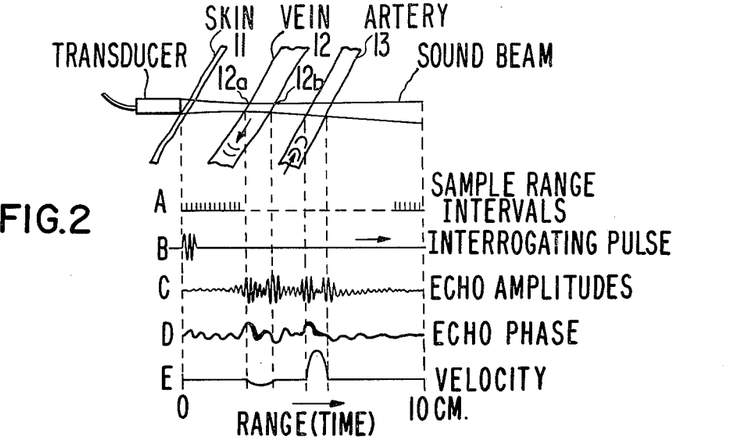
FIG. 2 is a graphical depiction of the various electrical signals transmitted, received and produced by the system of FIG. 1, plotted on a comparable time scale or spatial range scale, to illustrate the functioning of the system of FIG. 1.

A complete ultrasonic Doppler flowmeter system in accordance with the invention is illustrated in FIG. 1. Initially, means are provided for transmitting an RF ultrasonic pulse via a transducer 10 into the body of a patient whose internal fluid flow or blood vessel structure is desired to be examined. Associated therewith are means for receiving echos resulting from the reflections of the interrogating pulse set up by the internal tissue interfaces and scatterers, such as the blood flowing within the vessels under examination. FIG. 2 may be referred to to show the orientation of the transducer 10 with respect to the patient's skin 11, vein 12, and artery 13 below the skin. Transducer 10 is excited with radiofrequency energy by transmitter 14 operating at a typical frequency, of the order of four megahertz, under the influence of oscillator 16 to emit pulses of corresponding high frequency ultrasound. The transmitter is pulsed at a pulse repetition frequency of the order of 6.4 kilohertz, thus allowing an interval of some 160 microseconds between two consecutive interrogating pulses. The length of time travelled by sound within such 160 microsecond intervals, corresponds to roughly 10 centimeters, which defines the range of the instrument into the body from the transducer-skin interface within which echos can be picked up from structures of interest.

Line B of FIG. 2 plots this interrogation time, or the corresponding range, along the horizontal axis, out to 10 centimeters. Line B of FIG. 2 illustrates the initial interrogating burst as it starts out along the range into the body. As the interrogating pulse travels inwardly, it will excite return echo information tion, of amplitude and phase which depends on the degree of discontinuities encountered, and their motion. This is graphically illustrated by Line C of FIG. 2. It will be seen, for example, the echos emanating from the tissue interfaces at 12a at the outer wall of vein 12, as well as the similar interface at 12b at the inner vein wall, are very large in amplitude as compared to the echos set up by scattering from the blood flow within the vein. In actuality, the difference in amplitude may be as much as two orders of magnitude.

Such echo information, received back from the transducer 10 and transduced into corresponding electrical signals as illustrated in Line C, then is passed to the mixer-demodulator 20, where it is mixed with local oscillator signals, one differing in phase by 90° from the transmitter signal, by means of phase delay 21 and local oscillator 16. In this manner, two signals are in effect provided, the detecting original received signal carrying the echo information, and the orthogonal signal. This quadrature arrangement enables phase to be preserved, and enables the detection of the sign, whether negative or positive, of the Doppler velcity component by the sign detector circuit to be described below.

The mixer-demodulator 20 separates the original Doppler information carrying envelope of both the original and orthogonal RF echo signal, and then directs each of the quadrature demodulated signals to sample and hold units 23 and 24, respectively. Multiplexer 25 alternately switches between the two sample and holds to alternately present the demodulated echo signals of each channel to stationary canceler-filter 26, (which actually is duplicated in parallel to accommodate both of the orthogonal demodulated echo signals of each channel at the high sampling rate of the order of 1 sample per microsecond). Thus, with the aid of sample and hold units 23 and 24 and multiplexer 25, the demodulated echo signals are scanned into a plurality (here 128) of uniform time intervals or channels, as illustrated in line A of FIG. 2, with total time equal to the interval between successive interrogating pulses. Of course, each such channel or portion of the time interval between pulses also then corresponds to an interval of the 10 centimeter range within the patient's body which is under interrogation. The overall problem of detecting the position and magnitude of velocity changes within a patient's structure then is resolved into one of detecting the Doppler frequency change at the level associated with each of the channels of the range. The particular number of channels is not critical, and has been chosen for convenience, in view of the capabilities of the digital components, the sampling times, and the pulse repetition and ultrasound frequencies involved.

Figure 3:
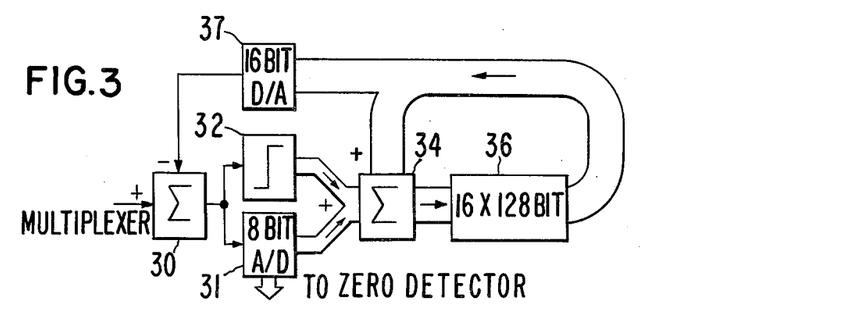
FIG. 3 is an electrical circuit block diagram of the improved filter-canceler of the Doppler system of FIG. 1, in accordance with the further aspects of the present invention.

The large amplitude "clutter" signals as mentioned above mask the lower amplitude signals from the moving fluid scatterers which contain the Doppler information sought to be detected. However, the influence of such clutter signals may be substantially mitigated by the use of stationary canceler-filter 26. This filter utilizes the fact that the clutter signals, being from stationary or quasi-stationary tissue interfaces, change little if at all from pulse to pulse, in contrast to the rapidly-changing smaller-amplitude signals from the moving fluid scatterers. The stationary canceler-filter of the present invention is illustrated in FIG. 3.

The filter includes an analog subtractor 30 which receives inputs from multiplexer 25 and which includes an output connected to both 8-bit analog/digital converter 31, and a Highest Active-Bit Detector 32, hereinafter the HABD 32. These two units both have outputs supplying a digital adder 34, while the A/D converter 31 also supplies its output to the zero crossing detector of FIG. 1. Adder 34 in turn inputs a storage unit 36, which may be a RAM. Storage 36 is a memory of 16 by 128-bit capacity, since 128 channels will have to be serviced, and for each, a 16-bit word capacity is provided. Storage 36 is connected both to 16-bit digital-to-analog converter 37 which in turn is connected to the second input of subtractor 30, and also supplies a second input of adder 34 with its output. The basic recursive nature of the operation can be readily appreciated from FIG. 3, but the finer points of the iterative process under which the filter operates, requires more detailed explanation of the operation of the filter.

In operation, the analog values within the sample and hold units 23 and 24 are directed by multiplexer 25 in turn for each of the channels into one input of subtractor 30. A representative one of such values for convenience may be termed $M_p$, that is, the echo values associated with a transmit or interrogating pulse p in a representative channel R. The immediately preceding value in that channel R, from the immediately preceding interrogating pulse $p-1$, is then $M_{p-1}$. Let us assume that the latter has been earlier processed by the filter, digitized, and is now stored in storage 36 of the filter. Note that in this particular case, the data path is 16 bits wide, which is approximately 100 decibels of dynamic range. It has been found that such a dynamic range is needed to resolve the Doppler information from background clutter. Thus, the digital/analog converter 37 is 16 bits in capacity. Because the operation of the filter will eliminate the need for the higher order bits by filtering the clutter, A/D converter 31 is of 8-bit capacity. Thus, the faster components of the echo signals, which have a spectral component above the stationary clutter, should be adequately serviced, in theory.

Now let us examine the basic and normal mode of operation for the recursive filter in channel R as echo information from a new interrogating pulse p is received. Upon presentation of the value $M_p$ to the positive input of analog subtractor 30, the previously stored value $M_{p-1}$ from storage 36 and previously associated with channel R is taken from the storage unit output, and presented to digital/analog converter 37. The latter then directs the information, now in analog form, to the negative input of analog subtractor 30, where it is subtracted from the already queueing value $M_p$ belonging to pulse p. Thus, the difference value $M_p - M_{p-1}$ is formed at the output of subtractor 30 and directed to analog to digital converter 31 and to the input of comparator 32. As will be explained below, the comparator's output is zero and it effectively is out of the circuit as long as the dynamic range of A/D converter 31 is not exceeded. Under this assumption, A/D converter 31 digitizes the difference value $(M_p - M_{p-1})$ whereupon the value is passed to the zero crossing detector of the FIG. 1 system as will be described, and also to one of the inputs of digital adder 34. Digital adder 34 through another of its inputs also receives the stored value $M_{p-1}$ from the output of storage 36. Also receiving the stored value $M_{p-1}$ from storage 36 is digital/analog converter 37, which thereafter passes it to the minus input of analog subtractor 30. Digital adder 34 then performs the addition $M_{p-1} + M_p - M_{p-1}$ of its input, resulting in the digital value $M_p$. The latter is then stored in storage unit 36 and thereupon becomes available to average against the next subsequent value $M_{p+1}$ for the same channel R, which value will result upon the occurrence of the next following interrogating pulse $p+1$. Thus, a recursive loop is described, and a means for cancelling the unwanted low frequency components by in effect tracking the portions of the signals which do not change between subsequent pulses and removing same, while digitizing the residual remaining small amplitude signal, which should be the Doppler component, at high speed.

It has been found that in any such filter system as thus far described without the benefit of HABD 32, and where the maximum number of bits in the digital data stream is N (any number such as 10, 14, 16 etc.), and the digitizing bit rate for the Doppler component at the A/D converter 31 is n (any number such as 4, 6, or 8 etc.), then the longest period in which the input value is not the same as the digital output is given by the expression $$2^{(N-n)}/f_{PRF}$$

where $f_{PRF}$ is the pulse repetition frequency, and $1/f_{PRF}$ is the corresponding time period of the repetition.

In this case, of course, this input value is the value of the echo signal for the channel being studied, and the digital output is the corresponding digital form of the echo signal, out of which the higher order stationary components have been filtered. The foregoing expression is then a measure of the "dead time" of the filter, during which the filter is not seeing useful small-amplitude Doppler-information-bearing signals from moving scatterers because of masking by a large clutter signal.

Another way of expressing the same type of concept is that if the filter is saturated by a large clutter signal of high order, equal to or surpassing its 16-bit capacity, the quantity $$2^{(N-n)}$$

gives the number of iterations which the recursive loop of the filter must perform in order to respond to the clutter signal and to eliminate same. Of course, the number of iterations is a measure of response time necessary to take care of such clutter signals. A system with as small a number of iterations as possible is highly desirable in terms of response time, and to eliminate dead time during which the filter is not reading useful Doppler information. Filters along the above-described lines, without the benefit of the action of HABD 32, have been found to have unacceptably long response times when faced with processing high-order or saturation-level clutter signals, as too often occurs in the real world, and thus, to be highly susceptible to problems in handling signals exceeding the dynamic range of the A/D converter.

It is instructive to appreciate the numbers of iterations necessary in such a system to handle a saturation signal. Let us assume, to simplify the analysis, that digital/analog converter 37 is of 7-bit capacity, while analog digital/converter 31 is only of 4-bit capacity. Thus, in the above "dead time" formula, $N=7$, and $n=4$ for this example. An incoming clutter signal saturating the system would then represent 128 counts, i.e., $2^7$, the highest number of counts handleable by the data lines. The A/D converter 31 would then be saturated with its maximum number of counts, or $2^4=16$. In accordance with the above mode of operation, A/D converter 31 would pass a count of 15 through adder 34 and into storage 36, whereupon it would return via D/A converter 38 to be subtracted from the 127 input count, to result in 112 counts residue. Another recursion would then take place, with D/A converter again inputting its maximum 15 count value into the loop and the now 30 counts in the storage would then be subtracted from the inputted 127, leaving 97 counts after the second iteration. Upon the third iteration, the memory would contain 45 counts which would then be subtracted from the still-saturation 127 input counts, still leaving 82 residue. It may be seen that the iterations would continue for 8 cycles, until the residual counts finally dropped below the 15 count dynamic capacity of A/D converter 31, in accordance with the above expression.

By contrast, it has been found that a unique and very marked improvement in dynamic range and response time, for a given number of bits resolution, can be obtained by the implementation of a system as above with HABD 32 used and positioned as described. In fact, the filter with HABD 32 functioning will only have a maximum number of iterations represented by the quantity:

$(N-n)$ rather than $2^{(N-n)}$ as is the case with the non-HABD-based system as described above. Similarly, the longest period over which Doppler information contained in the output of the fast A/D converter 31 may be lost, is now given by the quantity:

$(N-n)/f_{PRF}$ where $f_{PRF}$ is, as before, the pulse repetition frequency, N is the maximum number of bits in the data path, and n is the digitizing bit rate at A/D converter 31. The present system thus obviates the slow response heretofore typically seen with such filter/cancelers, and thus cuts the number of iterations, and consequently the dead time during which the filter does not respond to Doppler information, very drastically, especially for systems accommodating the higher dynamic ranges, resolutions and greater number of bits in the data path.

HABD 32 itself is structured to identify the highest active bit between the n-bit and the (N−1)-bit whenever the dynamic range of the fast n-bit A/D converter is exceeded. In the actual described embodiment, since $n=8$ and $N=16$, the comparator identifies the highest active bit between the 8th-bit and the 15th-bit whenever the 8-bit dynamic range of the A/D converter is exceeded by a saturation signal. This highest active bit is then fed into the digital adder 34, together with the saturated value output from the A/D converter 31, and the iteration by the recursive loop continues as above described until the dynamic range of A/D converter 31 is no longer exceeded.

In order to effect this performance, HABD 32 includes two sets of a like plurality of comparators, the plurality being given by the quantity $[N-(n+1)]$; in this case, seven comparators per set. One set of seven is for the positive signals, and one set is for the negative. Thus, HABD 32, like the analog/digital converter 31, is bipolar, that is the summation point in the recursive loop is consistent for both positive and negative signs, and sign magnitude consistency is maintained. In addition to these comparators, a logic circuit is included which monitors the output of the comparators and identifies the one with the largest positive or negative threshold, and thus the corresponding highest active bit.

It is instructive to extend the above simplified analysis of the iterations necessary to handle a saturation signal to the present system, as a rough measure of the improvement obtained as compared to earlier filters. We again assume the same conditions as previously, i.e., $N=7$ and $n=4$, an incoming saturation-level clutter signal of the maximum 127 count value, and thus saturation for the A/D converter again at a value of 15 counts. HABD 32 will detect and add the highest active bit between $N-1$ and n. In this case, $N-1-n=2$. Thus, the HABD is to detect the two upper bits (below the MSB), then present them to the adder along with the low order bits from A/D converter 31, which then go into storage 36 and are subtracted from the input signal in the recursive fashion as previously. The two upper bits in this case are represented by $2^6$, $2^5$, whose value is 63. Thus, the HABD and A/D converter deposit the value 63 counts into adder 34 and thus into storage 36. This value is then subtracted from the initial saturation input value of 128 counts, leaving a residue of 65 which is still greater than the dynamic range of 16 counts of A/D converter 31; thus the iteration continues. After another input of 63 counts to the memory, which is then subtracted from the residue of 65 counts, we are down to 2 counts, which is within the range of the A to D converter 31. Thus, within three iterations, as predicted from the aforementioned expression, $(N-n)$, the large-amplitude saturating signal has been eliminated and the filter is again operating within the dynamic range of the fast A/D converter 31. A significant reduction in the response time of the filter to large input signals is then manifested.

Figure 4A:
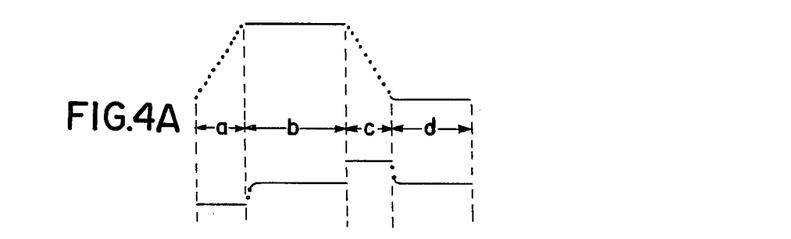
FIG. 4 is a graphical depiction of response time of the filter of FIG. 3, as compared to prior art filters.
Figure 4B:
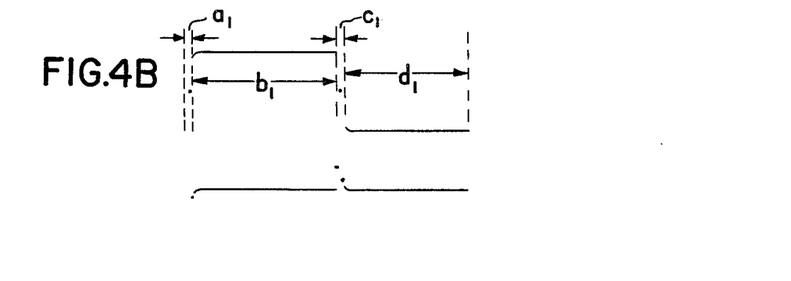

FIGS. 4A and 4B show the results of comparison between the response time of the instant system, and the response times of corresponding earlier filters without the improvements herein. In FIG. 4A, intervals a and c represent the times during which a filter without the present improvements recursively executes iterations upon reception of a large stationary echo signal component. These of course are also time periods during which any received Doppler information is being masked out. Intervals b and d then represent times after reception of large stationary components during which Doppler information is actually being processed. These intervals a and c represent "dead times" for the filter. The much improved situation for a filter in accordance with the invention is illustrated on a comparable scale in FIG. 4B. The dead times a and c after reception of a large stationary component are drastically reduced, leaving correspondingly much increased intervals b and d during which the filter sees Doppler information.

At this point in our description of the overall FIG. 1 system, we have arrived at the output of the canceler-filter 26, which output is in digital quadrature multiplexed binary offset code, and contains the Doppler information, with the stationary components eliminated, for each channel in turn and for both quadrature components. This signal is then passed to a zero crossing detector 48, which also includes a threshold noise eliminator in the form of a Schmitt trigger. The object is to detect the number of zero crossings which the Doppler signal undergoes over a period of time, which then gives a measure of the Doppler frequency, and hence, the velocity of the structures or fluids under observation. Working with the zero crossing detector is a flow velocity sign detector 50, which in turn is inputted by the zero detector and which then enables determination of the direction of the flow of the fluid under observation, that is, whether the flow is toward or away from the transducer.

Figure 5:
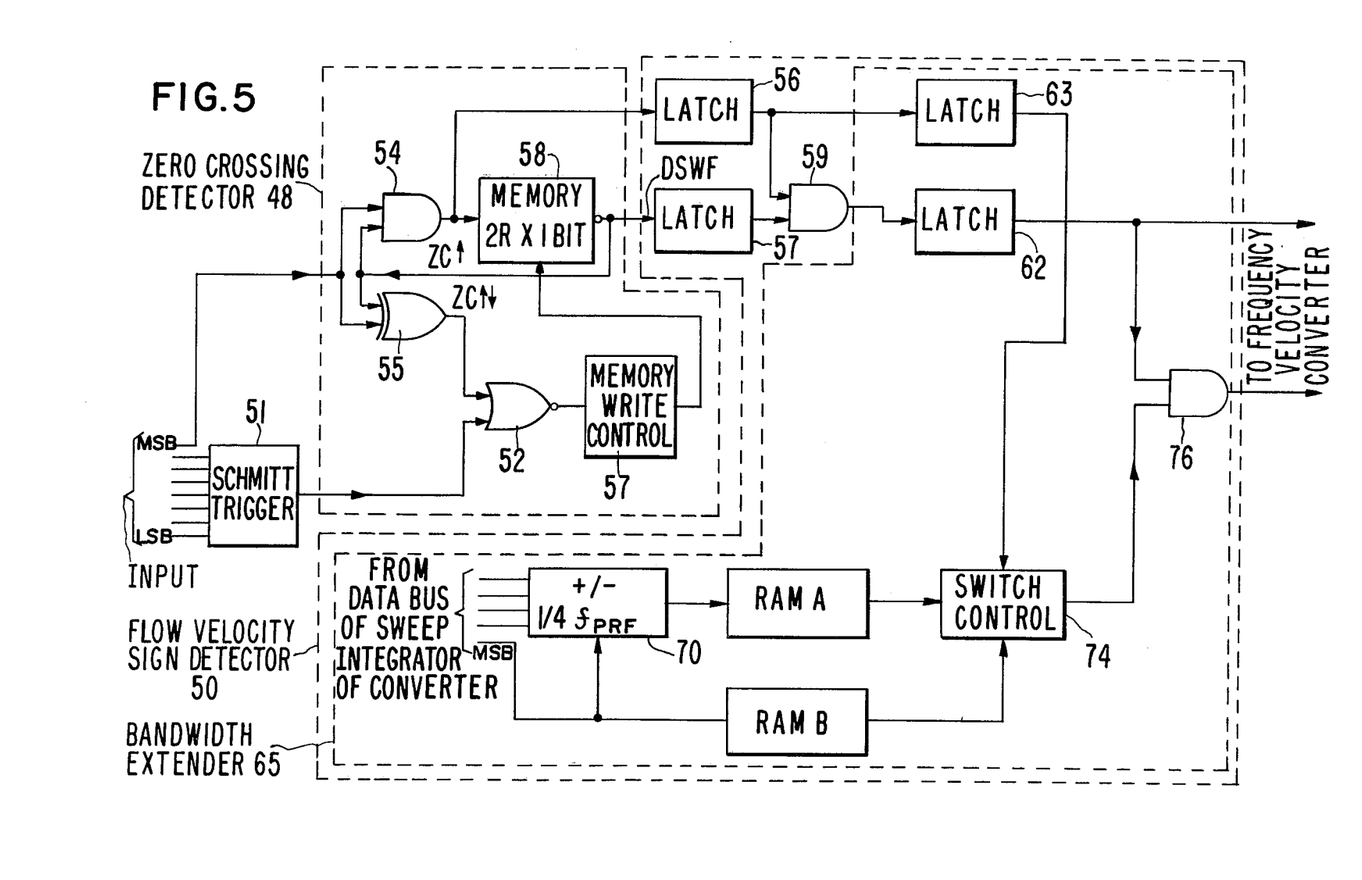
FIG. 5 is an electrical circuit block diagram of the improved zero detector and the improved sign detector of the Doppler system of FIG. 1, in accordance with another aspect of the present invention.

FIG. 5 shows both zero crossing detector 48 and sign detector 50 in more detail. With the incoming signal in binary offset form as described, the digital data bus for each channel may be truncated to a single synchronous pulse string with the aid of the Schmitt trigger 51, functioning as a threshold noise eliminator. As shown, the most significant bit (MSB) of the incoming signal, which is the sign bit, goes directly to zero crossing detector 48, while the remainder of the bits down to the least significant bit (LSB), are compared in the Schmitt trigger, which suppresses the false zero crossings within a preselected noise level by zeroing the less significant bits. If the value of the incoming signal is above the preselected noise level, an output is directed to one input of NOR gate 52.

Meanwhile, the most significant bit is directed to one of the inputs of AND gate 54, and one of the inputs of Exclusive OR gate 55. It will be noted that the Exclusive OR gate has its output connected to the other input of NOR gate 52, whose output is connected to memory write control 57, which in turn through a connection to the one-PRF-delay memory 58 controls the activation of the latter. Memory 58 has a capacity of 1-bit for each of twice the channels or range intervals, so that both of the orthogonal Doppler sub-channels may be accommodated. Inputting memory 58 is the output of AND gate 54, while the output of memory 58 is connected both to the remaining input of AND gate 54, as well as to the remaining input of Exclusive OR gate 55.

The incoming Doppler signal for each channel in turn, or more precisely the most significant bit or the sign bit, enters the zero cross detector at one of the the inputs of both gates 54 and 55. For convenience of description, we adopt the convention that a negative zero crossing is denoted by a logic "one", while a positive zero crossing is denoted by a logic "zero". The function of the Exclusive OR gate 55 is to compare the incoming input with the previously stored value from the preceding transmit or addressing pulse, which has been stored in memory 58 and is available at the remaining input of gate 55 (which is connected to the output of memory 58). If any change of state is seen by the gate, denoting the occurrence of a zero crossing, the gate will deliver an output to NOR gate 52. If no change in the channel under consideration is detected since the last pulse, no output results. Of course, the exclusive OR gate 55 delivers an output for each zero crossing occurrence, regardless of whether the crossing is a positive or negative one. Assuming that Schmitt trigger 51 has found the value of the incoming signal to be greater than the noise level, both inputs of NOR gate 52 will be activated, and thus NOR gate 52 triggers write memory control 57 with an output, which in turn activates memory 58.

Meanwhile, at AND gate 54, the determination is made whether or not the incoming information is a zero crossing in one predetermined direction. In this case, the circuit has been designed to monitor zero crossings in only the negative direction. This operation is accomplished by gate 54 comparing the incoming bit with the previously stored information from the memory reslting from the immediately preceding pulse. It should be noted that the output of the memory inverts the stored value prior to directing it to the input of AND gate 54. This results in the AND gate 54 delivering an output only where the previously stored value denoted a positive zero value, or a logic zero, and the incoming input is a logic one, denoting a negative value. If the truth table of the AND gate is considered, it will be seen that the output must be zero for all other inputs except for this particular coincidence.

Upon the detection of a negative zero crossing as just described, the resulting output of gate 54, a logic one, is then directed to the input of memory 58, to be written into the memory at a location corresponding to the range interval and orthogonal signal considered. It will be recalled that the memory write control simultaneously has activated the memory, since it has at the same time detected a zero crossing (of whatever sign). Thus, if the zero crossing turns out to be negative, as determined by gate 54, a logic one will be written into the memory, while if gate 54 does not so react to the zero crossing, and its output remains zero, a logic zero will be written into the memory, thus denoting that the crossing was a positive one. Thus, the memory tracks and stores both the occurrence of the zero crossing, as well as its sign, at the memory locations corresponding to the range interval, and also corresponding to which of the two orthogonal signals is under consideration.

As shown in the FIGURE, the zero cross detector has two outputs into the flow sign detector 50. One output is provided by the output of memory 58; it will be appreciated that such output as a function of time per channel has the form of a square wave ranging between zero and one, whose frequency is Doppler frequency of the corresponding range interval for the given channel under consideration. This Doppler Square Wave Frequency signal (or "DSWF signal") also is multiplexed to contain both quadrature subchannels A and B. The other output is taken from the output of AND gate 54; since it produces an output only when a zero crossing occurs in one given direction, here the negative direction, it generates a multiplexed data pulse train, at the Doppler Frequency. This one-way zero crossing signal or "ZC signal", also contains both orthogonal quadrature subchannels A and B.

The output from gate 54, which is indicative of zero crossings in one direction only, or the zero cross period, is inputted into the first latch 56 of flow sign detector 50. Similarly, the output from memory 58 is inputted into the second latch 57 of the flow sign detector. Latches 56 and 57 respectively only respond to opposite ones of the multiplexed orthogonal quadrature subchannels, respectively, since they act to synchronize same so that they may be compared by AND gate 59 to aid in determining flow direction. Thus, for example, subchannel A of the DSWF signal has its instantaneous value at a predetermined time registered on one of the latches, while subchannel B of the ZC signal at the same time has its instantaneous value at the same predetermined time registered on the other of the latches.

In this case, latch 56 handles the ZC signal, and has an output of a logic one whenever a zero crossing is detected in one given direction for its quadrature subchannel. At other times, the output of latch 56 is a logic zero. Latch 57, which handles the DSWF signal, yields a logic one output whenever any zero crossing is detected for its quadrature subchannel. A zero output indicates no zero crossing is detected. In this way, the heretofore serial orthogonal channel information may be compared, and the information of the square wave from memory 58 indicative of each of the zero crossings may be compared to the pulse strain from gate 54 showing only the crossings in one direction.

AND gate 59 then compares the latch outputs. The output of the gate will of course be zero unless both latches 56 and 57 have inputted a logic one. Accordingly, a zero output of gate 59 indicates the instantaneous direction is in one sense, while a one output indicates the instantaneous direction is in the opposite sense. Accordingly, one of the outputs may be thought of as leading, while the other may be thought of as lagging. Hence in one case, we will have identified a positive Doppler shift, while in the other case a negative Doppler shift is indicated.

As indicated in FIG. 1, the output of the flow sign detector is directed to a rather conventional frequency to velocity converter 60, which includes a sweep integrator in which the incoming pulses are added or subtracted, depending upon whether a positive or negative Doppler shift is being detected by the sign detector. This is implemented as follows: a first output of the flow sign detector is that from AND gate 59 (through latch 62). The second of the outputs is that from latch 56, as modified by the Doppler bandwidth extender circuit 65 portion (FIG. 5) of sign detector 50, as will be described below. As we have seen, the first output, which is a logic one or zero, correspondingly instructs converter 60 whether or not a zero crossing (of either sign) has occurred which must be counted in the channel under consideration. The second output, also a logic one or zero, correspondingly instructs the converter 60 whether to add or subtract any logic one pulses from a zero crossing incoming on the first output; in effect, it thus is a sign bit. The converter 60 then accumulates such counts for a predetermined time (here 20 milliseconds) for each of the channels or range levels, and then produces a set of digital values proportional to the velocity for each channel. The converter is then zeroed, and the accumulation of counts begins again.

In actuality, however, the above simplified explanation of sign detector 50 does not take into account a major difficulty, nor the present invention's solution for it in the form of bandwidth extender 65. As the sweep integrator of converter 60 accumulates counts for each channel as aforesaid, at some point the total in absolute terms may exceed, at least for some of the channels, the value of:

$$\tfrac{1}{4} f_{PRF}$$

This important value is the well-known Nyquist criterion for quadrature multiplexed sampled systems. (Since we are dealing with the sampling of quadrature signals, the usual Nyquist criterion must be halved.) If the accumulated count of a channel indicates a Doppler frequency above this criterion of one-quarter the pulse repetition frequency, it is well-known that phase information can no longer be preserved. In other words, the above-mentioned sign bit, the second input from sign detector 50 to the converter 60, by which the converter is instructed whether to add or subtract the zero crossing pulse into the accumulating total, is no longer reliable. Then, although the fact that a zero crossing took place is reliably known to the converter, the direction of the crossing is not. Rather than continue to permit the use of the instantaneous direction, bandwidth extender circuit 65 instead causes a substitute sign to be used which is determined on the basis of the immediate history of the direction of the count prior to its exceeding the Nyquist criterion. Bandwidth extender 65 is so called since it then, in effect, extends the bandwidth of the system to accommodate Doppler bandwidths beyond the Nyquist criterion.

The circuit operates as follows. As may be seen in FIG. 1 and in detail in FIG. 3, the output data bus of converter 60 is monitored by circuit 65, with the most significant bit (MSB), which is the sign bit, going to RAM B, of 1 by 128-bit capacity, while the remaining bits, which represent the absolute value of the instantaneous channel velocity, enter +/− logic 70, which compares the counts corresponding to this velocity (whether positive or negative), with the level of counts representative of the predetermined Nyquist criterion. At the same time, the current sign of the velocity is placed in RAM B in the appropriate location for that channel. Upon logic 70 indicating that the Nyquist criterion is exceeded, it produces a pulse which is stored in RAM A in the appropriate location for that channel. These operations are done for each accumulation period (here 20 milliseconds) for every channel location.

Switch control 74 has three inputs, one each from RAM A, RAM B and Latch 62, in order to monitor the occurrence of a count from RAM A indicating an excursion beyond the Nyquist criterion in the converter 60. Latch 62 which as stated above receives the input of AND gate 59, and latch 63, which receive the input from latch 56, operate to synchronize the corresponding Doppler frequency signal and the time of a zero cross. Thus, at each channel, switch 74 interrogates the corresponding RAM A location. If a value is stored, then the Nyquist criteria has been exceeded, either in the negative or positive direction. Normally, without such an occurrence, switch 74 merely completes a path between latch 62 and output AND gate 76 to the sign detector, so that latch 62 delivers to output AND 76 the instantaneous sign bit. Reliable sign information is thereby transmitted, since with the switch not having detected a pulse from RAM A, the Nyquist criteria will not have been exceeded.

However, upon switch 74 receiving such a pulse from RAM A, it instead passes to output AND gate 76 the stored sign from RAM B, which is the last reliable sign information prior to the accumulated count for the channel exceeding the Nyquist criterion. The output AND gate 76, which is also inputted by latch 62, synchronizes the Doppler frequency data flow with this sign information. Of course, when the Doppler frequency for the channel, and the corresponding counts, return to below the critical Nyquist value, switch 74 again couples the instantaneous sign information back into output AND gate 76. In this manner, the sweep integrator of converter 60 is always supplied with a reliable sign by which to determine whether to add or subtract the incoming zero crossing counts, even when the Doppler bandwidth exceeds the Nyquist criterion. It may be said that in effect, the bandwidth of the system is thereby extended.

The final stage of the system is buffer/output 80, which receives the velocity signal from each channel from converter 60, and stores same, or directs the signals to an output digital analog convertor and thence to a video display means. With the aid of typical display and microcomputer aids, many different modalities can be effected, for example, two dimensional flow maps and flow pulse calculations. The system is capable of responding to rapid changes in the velocity of a blood or other fluid stream under observation, without being overly sensitive to noise and sporadic interferences, and provides a large dynamic range whereby the true magnitudes of the Doppler velocities are properly preserved. Response times for given levels of resolution have been substantially improved, the influence of clutter signals has been substantially diminished, and accuracy in the display of Doppler velocities, particularly those corresponding to Doppler frequencies exceeding the Nyquist criterion, has been substantially improved.

We claim:

1. An ultrasonic Doppler system for measuring velocity of fluids moving within internal patient structures, comprising:
    means for transmitting an acoustic beam of addressing pulses of ultrasonic frequency acoustic waves into said patient structure, and receiving the reflected acoustic echo energy from both stationary and moving acoustic scatterers within the path of said beam and demodulating same into corresponding electrical signals containing both Doppler and stationary echo information;
    means for sampling said echo signals into a plurality of channels, each corresponding to a portion of the time between said addressing pulses;
    means for determining from the digital form of said Doppler echo information, the velocity of said fluids, said means including a zero cross detector and a flow velocity sign detector; and
    filter canceler means receiving signals from said means for sampling and supplying an output to said velocity determining means, said filter in turn processing each of said channels, said filter employing a recursive loop including a digital memory for comparing the echo signals from each addressing pulse with its immediate echo signal predecessor, a subtractor to subtract any unchanged non-Doppler components for each channel, and an analog to digital converter for rapidly digitizing the remaining changing components of said echo signal, said means including comparator means in parallel with said analog to digital converter for identifying the highest active digital bit between the digital dynamic range of bits in the data path of the incoming echo signals, and the dynamic range of the analog to digital converter, said comparator means providing said highest active bit to be added along with the output of said analog to digital converter into said memory, so that upon comparison of the output of said memory with the incoming echo signal for each given channel and subtraction therefrom, and subsequent iterations thereof, the number of iterations is decreased, and the response time is correspondingly improved for large stationary signals.

2. An ultrasonic Doppler system as in claim 1, in which said comparator means includes two sets of a like plurality of comparison circuits, one set being for the positive signals, the other set being for the negative signals, and logic means monitoring the output of said comparison circuits and identifying the one of said comparison circuits having the largest absolute value threshold, the corresponding bit being said highest active bit.

3. An ultrasonic Doppler system as in claim 2, which said digital dynamic range is of N bits capacity, said analog to digital converter is of n bits capacity, and in which said plurality of comparators in each of said sets is given by the expression:

$$N-(n+1)$$

4. An ultrasonic Doppler system as in claim 3 which further includes a digital to analog converter between the output of said digital memory and an input of said subtractor, said digital to analog converter being of N bits capacity.

5. An ultrasonic Doppler system as in claim 3, in which said comparator means is in parallel with said analog to digital converter, and in which said comparator means has a nonzero output only when the dynamic range of said analog to digital converter is exceeded.

6. An ultrasonic Doppler system as in claim 5, in which said memory for each channel stores data due both to the output of said analog to digital converter, and the output of said comparator, and in which said subtractor is an analog subtractor having an input receiving an incoming signal due to a new addressing pulse, and another input receiving said stored data resulting from the previous addressing pulse, said subtractor output up with supplying both said comparator and said analog to digital converter, said stored data comprising both the output from said comparator and from said analog to digital converter being thereby subtracted from said incoming signal, whereby further iterations over said loop are substantially reduced.

7. A sampled ultrasonic Doppler system for measuring the velocity of fluids moving within internal body structures comprising:
    means for transmitting an acoustic beam of addressing pulses of ultrasonic frequency acoustic waves having a regular phase repetition rate into said body structure and for receiving the acoustic echo energy from both stationary and moving acoustic scatterers within the path of said beam, and converting same into corresponding electrical signals;
    means for demodulating said echo signals into quadrature echo signals, said quadrature signals containing both Doppler and stationary echo information;
    means for sampling said echo signals into a plurality of equal channels, each corresponding to a portion of the time between said addressing pulses;
    filter means accepting and digitizing said echo signals for each channel and cancelling therefrom any stationary non-Doppler information;
    means for determining, from the remaining signal comprising Doppler echo information in digital form, the zero crossings in one direction of said Doppler information-bearing signal to obtain the Doppler frequency for each channel;

means for determining from said Doppler frequency information, and information as to whether the sign of the Doppler shift is positive or negative, the Doppler velocity for each channel, said means including means accumulating digital counts representative of said zero crossings; and means for determining the sign of said Doppler shift, and supplying said information to said means for determining velocity, including means for comparing the quadrature components of said quadrature echo signals to determine the instantaneous sign of said Doppler frequency shift for each channel, and means for comparing said accumulating counts against a predetermined frequency, and upon said counts exceeding the value corresponding to said predetermined frequency, substituting the sign which was determined just prior to exceeding said value, in preference to said instantaneous sign, whereby the accuracy of said Doppler velocity-determining means is improved.

8. A sample ultrasonic Doppler system as in claim 7, in which said predetermined frequency is the Nyquist criterion of one-quarter the interrogating pulse repetition rate for quadrature multiplexed sampled systems.

9. A sample ultrasonic Doppler system as in claim 7, in which said means for determining the Doppler shift sign includes a first memory storing a representation of the current sign of the Doppler velocity, a second memory, logic means to compare the absolute value of said accumulating counts with said predetermined frequency, and causing said second memory to store an indication if said frequency is exceeded in any channel, switch means receiving both signal representing said instantaneous sign, and a signal from said second memory indication to substitute said stored sign for said instantaneous sign as an input into said means for determining the Doppler velocity.

10. An ultrasonic Doppler system for measuring velocity of fluids moving within internal patient structures comprising:

means for transmitting an acoustic beam of addressing pulses of ultrasonic frequency acoustic waves having a regular pulse repetition rate into said patient structure, and receiving the reflected acoustic echo energy from both stationary and moving acoustic scatterers within the path of said beam, and demodulating same into quadrature electrical signals containing both Doppler and stationary echo information;

means for sampling said echo signals into a plurality of equal channels, each corresponding to a portion of the time between said addressing pulses;

means for determining from the digital form of said Doppler echo information, the velocity of said fluids;

filter canceller means receiving signals from said means for sampling, and supplying an output to said velocity determining means, said filter in turn processing each of said channels, said filter employing a recursive loop including a digital memory for comparing the echo signals from each addressing pulse with its intermediate echo signal precedessor, a subtractor to subtract any unchanged non-Doppler components for each channel, and an analog-to-digital converter for rapidly digitizing the remaining changing components of said echo signal, said means including comparator means in parallel with said analog-to-digital converter for identifying the highest active digital bit between the digital dynamic range of bids in the data path of the incoming echo signals, and the dynamic range of the analog-to-digital converter, said comparator means providing said highest active bit to be added along with the output of said analog-to-digital converter into said memory, so that upon comparison of the output of said memory with the incoming echo signal for each given channel and subtraction therefrom, and subsequent iterations thereof, the number of iterations is decreased;

means included in said velocity determining means for determining from said remaining changing components of said signal in digital form, the zero crossing in one direction to obtain the Doppler frequency for each channel;

means included in said velocity determining means for determining from said Doppler frequency information, and information as to whether the sign of the Doppler shift is positive or negative, the Doppler frequency for each channel, said means including means accumulating digital counts representative of said zero crossing; and means for determining the sign of said Doppler shift and supplying said information to said means for determining velocity, including means for comparing the quadrature components of said quadrature signals to determine the instantaneous sign of said Doppler frequency shift for each channel, and means for comparing said accumulating counts against a predetermined frequency, and upon said counts exceeding the value corresponding to said predetermined frequency, substituting the sign which was determined just prior to exceeding said value, in preference to said instantaneous sign.

* * * * *